United States Patent [19]

McLachlan

[11] B 4,014,897
[45] Mar. 29, 1977

[54] PROCESS FOR PREPARING CYCLICDICARBOXIMIDO-SUBSTITUTED PHOSPHONOTHIOATES

[75] Inventor: Ian McLachlan, King's Lynn, England

[73] Assignee: The Dow Chemical Company, Midland, Mich.

[22] Filed: Oct. 7, 1974

[21] Appl. No.: 512,779

[44] Published under the second Trial Voluntary Protest Program on April 13, 1976 as document No. B 512,779.

[30] Foreign Application Priority Data

Oct. 23, 1973  United Kingdom ............ 49325/73

[52] U.S. Cl. ............................................ 260/326 E
[51] Int. Cl.² ...................................... C07D 209/48
[58] Field of Search ................................ 260/326 E
[56] References Cited

UNITED STATES PATENTS 3,336,188  8/1967  Tolkmith et al. ............... 260/326 E
3,803,167  4/1974  Senkbeil ......................... 260/326 E
3,853,909  12/1974  Senkbeil ......................... 260/326 E Primary Examiner—Lewis Gotts
Assistant Examiner—S. P. Williams
Attorney, Agent, or Firm—S. Preston Jones; C. Kenneth Bjork

[57] ABSTRACT

Cyclicdicarboximido-substituted phosphonothioates corresponding to the formula

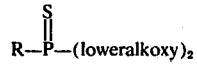

wherein R represents phthalimido, monomethyl substituted phthalimido, 4-cyclohexene-1,2-dicarboximido or monomethyl substituted 4-cyclohexene-1,2,-dicarboximido are prepared by a method which comprises reacting an appropriate O,O-diloweralkyl phosphorochloridothioate with an appropriate N-alkali metal cyclicdicarboximide reactant in the presence of a catalytic amount of a 1-(loweralkyl)imidazole and an inert tertiary alcohol as a reaction medium.

6 Claims, No Drawings

PROCESS FOR PREPARING CYCLICDICARBOXIMIDO-SUBSTITUTED PHOSPHONOTHIOATES

BACKGROUND OF THE INVENTION

This invention relates to an improved method for preparing cyclicdicarboximido-substituted phosphonothioates corresponding to the general formula (I)

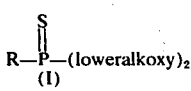

wherein in this and succeeding formula, R represents phthalimido

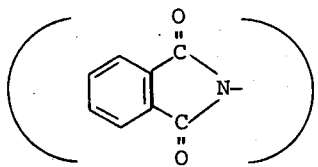

monomethyl substituted phthalimido

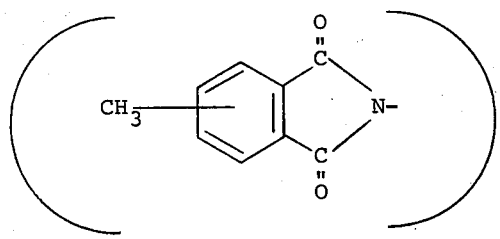

4-cyclohexene-1,2-dicarboximido

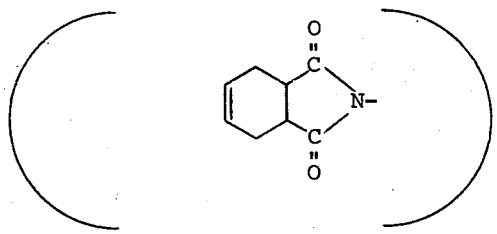

and monomethyl substituted 4-cyclohexene-1,2-dicarboximido

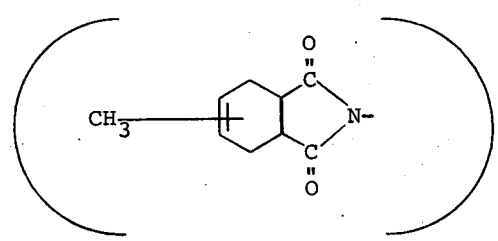

In the present specification and claims, the term "loweralkoxy" refers to alkoxy radicals of from 1 to 4 carbon atoms, inclusive. Such radicals would be for example, methoxy, ethoxy, n-propoxy, isopropoxy, n-butoxy, secondary butoxy and tertiary butoxy. It is to be understood that the two loweralkoxy radicals may be the same or different.

In the present specification and claims, the term "loweralkyl" refers to alkyl radicals of from 1 to 4 carbon atoms, inclusive. Such radicals would be for example, methyl, ethyl, n-propyl, isopropyl, n-butyl, secondary butyl and tertiary butyl.

Compounds of the above formula and methods for their preparation as well as a teaching of their utility as pesticides and as active toxicants in compositions for the control of insect, mite, helminth, plant, fungal and bacterial organisms are described in U.S. Pat. Nos. 3,336,188 and 3,450,713. The method taught by these references basically entails the reaction of an N-alkali metal derivative of a cyclicdicarboximido compound with an O,O-dialkylphosphorochloridothioate in the presence of an inert amido reaction medium such as, for example, N-methyl-2-pyrrolidone, dimethylformamide, hexamethylphosphoramide, N-acetylmorpholine and dimethylacetamide.

Another method of preparing the compounds of the present invention is taught in U.S. Pat. No. 3,399,213 wherein an alkali metal phosphoroamidothioate of the formula

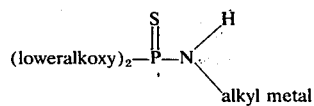

is reacted with a cyclicdicarboxylic anhydride of the formula

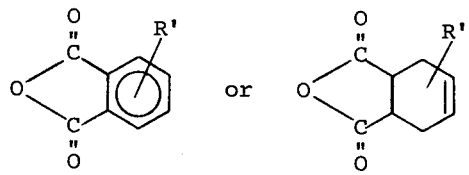

wherein R' is hydrogen or a variety of other substituents, in the presence of an inert liquid reaction medium followed by the treatment of the product so produced with a ring-closing reactant such as phosphorus or sulfur based acid halides or an anhydride of an organic mono-, di-, or polycarboxylic acid.

While the above-described processes are effective to produce the compounds they are not entirely satisfactory because of their low yield and new and improved processes are continually being sought.

SUMMARY OF THE INVENTION

It has now been found that the cyclicdicarboximido-substituted phosphonothioates of formula I can be produced in high yields sufficient to warrant economical commercialization and in a novel process by reacting a phosphorochloridothioate of the formula

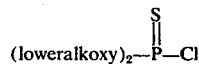

with an N-alkali metal salt of a cyclicdicarboximide reactant of the formula

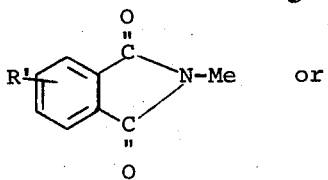

or

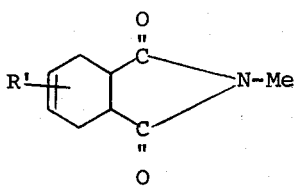

wherein R' is hydrogen or methyl and Me is sodium or potassium at a temperature of from about 0° to about 100°C. in the presence of a catalytic amount of a 1-(loweralkyl)imidazole and a tertiary alcohol as a solvent or reaction medium.

Representative compounds embraced by formula I and which may be prepared by the process disclosed and claimed herein, include:

O,O-dimethyl phthalimidophosphonothioate;
O-ethyl O-methyl phthalimidophosphonothioate;
O,O-diethyl phthalimidophosphonothioate;
O,O-di-n-butyl phthalimidophosphonothioate;
O-ethyl O-isopropyl (4-cyclohexene-1,2-dicarboximido)phosphonothioate;
O,O-di-n-propyl phthalimidophosphonothioate;
O-secondary-butyl O-methyl phthalimidophosphonothioate;
O,O-di-tertiary-butyl phthalimidophosphonothioate;
O-ethyl O-n-propyl (4-cyclohexene-1,2-dicarboximido)phosphonothioate;
O-ethyl O-n-propyl phthalimidophosphonothioate;
O,O-dimethyl (4-methyl-4-cyclohexene-1,2-dicarboximido)phosphonothioate;
O,O-di-n-propyl (4-cyclohexene-1,2-dicarboximido)phosphonothioate;
O,O-dimethyl (4-cyclohexene-1,2-dicarboximido)phosphonothioate;
O,O-diethyl (4-methylphthalimido)phosphonothioate;
O,O-di-n-butyl (3-methylphthalimido)phosphonothioate;
O,O-diisopropyl phthalimidophosphonothioate;
O,O-dimethyl (3-methylphthalimido)phosphonothioate;
O,O-dimethyl (4-methylphthalimido)phosphonothioate;
O,O-diethyl (3-methylphtalimido)phosphonothioate;
O,O-diisobutyl phthalimidophosphonothioate;
O,O-dimethyl (3-methyl-4-cyclohexene-1,2-dicarboximido)phosphonothioate; and
O,O-diethyl (4-methyl-4-cyclohexene-1,2-dicarboximido)phosphonothioate.

The critical features of the present process are in the use of a 1-(loweralkyl)imidazole as a catalyst and in the use of a tertiary alcohol as a solvent or reaction medium. The absence of either of these components drastically reduces the yield of the desired product.

The amount of the 1-(loweralkyl)imidazole employed, is that amount which allows the compound to act as a catalyst. This compound usually is employed in an amount of from about 0.01 to about 10 mole percent by weight based on the weight of the N-alkali metal cyclicdicarboximide reactant and preferably from about 1 to about 5 mole percent.

While the amount of the solvent employed is not critical, it has been found desirable to employ the solvent in an amount of from about 0.2 up to about 10 or more moles of the tertiary alcohol solvent per mole of the N-alkali metal cyclicdicarboximide reactant. In addition to the use of the tertiary alcohol as a solvent, it has been found that a co-solvent system can be also employed. The cosolvents employed are inert solvents which do not interfere with the action of the catalyst and tertiary alcohol. The specific co-solvent employed is not critical and the only limitation as to the solvent is that it is inert under the reaction conditions employed. Representative inert co-solvents include hydrocarbons such as, for example, heptane, hexane, benzene, xylene and cyclohexane and halohydrocarbons such as, for example, carbon tetrachloride, chloroform and methylene chloride. When one of the above co-solvents is employed it is usually employed in an amount of from about ½ to about 20 moles of the co-solvent per mole of the tertiary alcohol.

Representative 1-(loweralkyl)imidazoles which can be employed in the present method include, 1-methyl imidazole, 1-ethyl imidazole, 1-n-propyl imidazole, 1-isopropyl imidazole, 1-n-butyl imidazole, 1-sec.-butyl imidazole and 1-t-butyl imidazole.

Representative tertiary alcohols useful as the solvent or reaction medium in the present process are the tertiary aliphatic alcohols including for example, tertiary-butyl alcohol, tertiary-amyl alcohol and 3-methyl-3-amyl alcohol; and the tertiary aromatic alcohols such as, for example, triphenyl carbinol.

Representative phosphorochloridothioate reactants include, O,O-dimethyl phosphorochloridothioate, O,O-diethyl phosphorochloridothioate, O-secondary butyl O-methyl phosphorochloridothioate, O,O-di-n-butyl phosphorochloridothioate, O,O-diisopropyl phosphorochloridothioate, O-ethyl O-methyl phosphorochloridothioate, O-ethyl O-isopropyl phosphorochloridothioate, O,O-di-n-propyl phosphorochloridothioate, O,O-di-tertiary-butyl phosphorochloridothioate, O,O-diisobutyl phosphorochloridothioate and O-tertiary-butyl O-n-propyl phosphorochloridothioate.

Representative N-alkali metal cyclicdicarboximide reactants include the N-sodium and potassium derivatives of phthalimide, 3-methylphthalimide, 4-methylphthalimide, 4-cyclohexene-1,2-dicarboximide, 3-methyl-4-cyclohexene-1,2-dicarboximide, and 4-methyl-4-cyclohexene-1,2-dicarboximide.

The desirable results of the present invention are obtained by reacting the lower alkoxy phosphorochloridothioate reactant and the N-alkali metal cyclicdicarboximide reactant with agitation, in the presence of the tertiary alcohol solvent and the 1-(loweralkyl)imidazole catalyst.

Upon completion of the reaction, the desired product can be separated from the reaction mixture by first quenching the reaction mixture, such as, by pouring the reaction mixture into water, adding additional solvent to the mixture followed by heating the mixture from about 60° to about 70°C. The aqueous phase is separated and the organic phase containing the crude product is washed with water and cooled to about 0°C. The product is recovered by conventional separatory techniques such as, centrifugation, decantation or solvent evaporation. The product can be further purified, if desired, by solvent recrystallization followed by drying.

If no co-solvent has been employed, the product can be separated by quenching the reaction medium with water and separating the crude product by filtration. The crude product can be further purified by dissolving it in one of the above-identified co-solvents, heating the mixture to reflux followed by the removal of any insoluble material by hot filtration. The solvent-crude product mixture is cooled to about 0°C. and the product is recovered therefrom by conventional separatory techniques such as, filtration, centrifugation, decantation or solvent evaporation. The product can be further purified, if desired, by solvent recrystallization followed by drying.

It is to be understood that the specific mode of product separation is not critical and other conventional separatory procedures can be employed.

DESCRIPTION OF SOME PREFERRED EMBODIMENTS

In order that the present invention may be more fully understood, the following examples are given primarily by way of illustration and should not be construed as limitations upon the overall scope of the present invention.

EXAMPLE 1

O,O-Diethyl phthalimidophosphonothioate

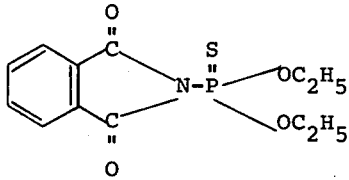

To an agitating mixture comprising 187 pounds (2.53 pound moles) of tertiary-butyl alcohol and 563 pounds (6.53 pound moles) of hexane was added 330 pounds (1.78 pound moles) of potassium phthalimide and 6 pounds (0.073 pound mole; 4.1 mole percent based on potassium phthalimide) of 1-methyl imidazole. This mixture was heated to 40°–45°C. and thereafter 370 pounds (1.96 pound moles) of O,O-diethyl phosphonochloridothioate was added over a period of about 2 hours. After a reaction period of 4 hours, the reaction mixture was quenched with water and additional hexane added. The mixture was heated to 60°–70°C. and the aqueous phase removed. The mixture was water washed for a total of 4 washes and cooled to 0°C. The crude O,O-diethyl phthalimidophosphonothioate product was recovered by centrifugation and the product purified by recrystallization from cold hexane and dried in a vacuum oven at 40°C. The product which was recovered in a yield of 85 percent of theoretical, melted at 81°–83°C. and was about 99 percent pure.

An additional run was carried out as follows:

To an agitating mixture comprising 896 pounds (12.0 pounds moles) of tertiary-butyl alcohol and 6 pounds of 1-methyl imidazole (0.073 pound mole; 4.1 mole percent based on potassium phtahalimide) was added 330 pounds (1.78 pound moles) of potassium phthalimide. This mixture was heated to 40°–45°C. and thereafter 370 pounds (1.96 pound moles) of O,O-diethyl phosphorochloridothioate was added over a period of about 2 hours. After a reaction period of 4 hours, the reaction mixture was quenched with water and the crude O,O-diethyl phthalimidophosphonothioate product was recovered by filtration. The product was purified by dissolving it in 1850 pounds of hexane and this mixture was heated to reflux and filtered hot to remove the insoluble by-products which formed. The filtrate was cooled to 0°C. and the desired purified product which crystallized upon cooling was recovered by centrifugation. The product was washed with cold hexane and dried in a vacuum oven at 40°C. The product was ~ 99 percent pure and was obtained in a yield of ~ 85 percent of theoretical.

Following the general procuedure of Example 1, employing various 1-(loweralkyl)imidazoles as a catalyst and the appropriate N-alkali metal cyclicdicarboximide and O,O-diloweralkyl phosphorochloridothioate reactants, the following cyclicdicarboximide phosphonothioates are prepared.

O,O-dimethyl phthalimidophosphonothioate melting at 126.5°–128°C. by reacting sodium phthalimide with O,O-dimethyl phosphonochloridothioate in the presence of 1-ethyl imidazole, tertiary-amyl alcohol and benzene.

O-ethyl O-methyl phthalimidophosphonothioate having a molecular weight of 285.3 by reacting sodium phthalimide with O-ethyl O-methyl phosphorochloridothioate in the presence of 1-n-propyl imidazole, tertiary-butyl alcohol and methylene chloride.

O,O-di-n-butyl phthalimidophosphonothioate having a refractive index N 25/D of 1.5340 and a molecular weight of 355.4 by reacting potassium phthalimide with O,O-di-n-butyl phosphorochloridothioate in the presence of 1-t-butyl imidazole, tertiary-butyl alcohol and xylene.

O,O-diethyl (4-cyclohexene-1,2, dicarboximido) phosphonothioate having a refractive index N 25/D of 1.5205 by reacting the sodium derivative of 4-cyclohexene-1,2-dicarboximide with O,O-diethyl phosphorochloridothioate in the presence of 1-isopropyl imidazole and tertiary-butyl alcohol. O,O-di-n-propyl phthalimidophosphonothioate melting, at 52°–53°C. by reacting sodium phthalimide with O,O-di-n-propyl phosphorochloridothioate in the presence of 1-sec-butyl imidazole triphenylcarbinol.

O,O-di-n-propyl (4-cyclohexene-1,2-dicarboximido) phosphonothioate having a molecular weight of 331.4 by reacting the potassium derivative of 4-cyclohexene-1,2-dicarboximide with O,O-di-n-propyl phosphorochloridothioate in the presence of 1-n-butyl imidazole, tertiary-amyl alcohol and cyclohexane.

Following the general procedures outlined above the following addition compounds are prepared.

O-ethyl O-isopropyl (4-cyclohexene-1,2-dicarboximido)phosphonothioate having a molecular weight of 317.4;

O,O-diethyl (4-methyl-4-cyclohexene-1,2-dicarboximido)phosphonothioate, an oil having an actual nitrogen content of 4.69 percent compared to the theoretical nitrogen content of 4.42 percent;

O,O-dimethyl (4-methyl-4-cyclohexene-1,2-dicarboximido)phosphonothioate melting at 40°–41.5°C.;

O,O-dimethyl (4-cyclohexene-1,2-dicarboximido) phosphonothioate having a molecular weight of 275.3;

O-ethyl O-n-propyl (4-cyclohexene-1,2-dicarboximido)phosphonothioate having a molecular weight of 317.4;

O,O-diethyl (4-methylphthalimido)phosphonothioate having a melting point of 69.5°–70°C.;

O,O-diisopropyl phthalimidophosphonothioate melting at 77°–81°C.;

O,O-dimethyl (3-methyl-4-cyclohexene-1,2-dicarboximido)phosphonothioate having a molecular weight of 289.2;

O,O-diisobutyl phthalimidophosphonothioate having a melting point of 38°–41°C.;

O,O-dimethyl (4-methylphthalimido)phosphonothioate having a molecular weight of 285.3; and O-secondary-butyl O-methyl phthalimidophosphonothioate having a molecular weight of 313.3.

PREPARATION OF STARTING MATERIALS

The N-alkali metal derivatives of the cyclicdicarboximido compounds employed as starting materials can be prepared by known procedures as taught in U.S. Pat. No. 3,450,713 wherein a cyclicdicarboximido compound of the formula H—R is reacted with an alkali metal hydroxide, and the alkali metal derivative of the dicarboximido compound separated from the reaction mixture.

The diloweralkoxy phosphorochloridothioates employed as starting materials are known compounds and can be prepared by known procedures. For example a thiophosphoryl chloride corresponding to the formula

is reacted successfully in either order or simultaneously with a compound having the formula loweralkoxy-H. Good results are obtained when employing the reactants in amounts which represent equimolecular proportions. When both of the loweralkoxy-H reactants are to be the same, good results are obtained when employing two molecular proportions of such reactant and one molecular proportion of thiophosphoryl chloride.

The reaction is carried out in the presence of an acid binding agent such as, for example, an organic tertiary amine compound. Conveniently the reaction is carried out in an inert organic liquid as reaction medium such as, for example, diethyl ether, benzene, carbon tetrachloride or methylene chloride.

What is claimed is:

1. A process for preparing cyclicdicarboximido phosphonothioates corresponding to the formula

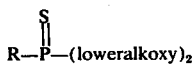

wherein R represents phthalimido, mono-methyl phthalimido, 4-cyclohexene-1,2-dicarboximido or mono-methyl-4-cyclohexene-1,2-carboximido which comprises reacting a phosphorochloridothioate corresponding to the formula

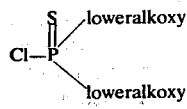

with an N-alkali-metal cyclicdicarboximide corresponding to the formula

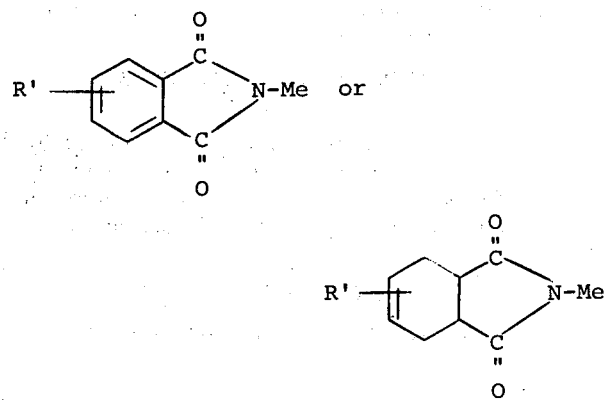

wherein R' represents hydrogen or methyl and Me represents sodium or potassium at a temperature of from about 0° to about 100°C. in the presence of an inert tertiary alcohol solvent and a catalytic amount of a 1-(loweralkyl)imidazole.

2. The process as defined in claim 1 wherein the temperature is in the range of from about 20° to about 50°C., and the inert tertiary alcohol is tertiary-butyl alcohol.

3. The process as defined in claim 2 wherein the cyclicdicarboximido phosphonothioate prepared is O,O-diethyl phthalimidophosphonothioate.

4. The process as defined in claim 2 wherein the 1-(loweralkyl)imidazole is present in an amount of from about 0.01 to about 10 mole percent by weight based on the weight of the N-alkali metal cyclodicarboximide reactant.

5. The process as defined in claim 2 wherein the tertiarybutyl alcohol solvent is in admixture with an inert co-solvent.

6. The process as defined in claim 5 wherein the inert co-solvent is hexane.

* * * * *